United States Patent [19]

Meilland

[11] Patent Number: Plant 7,622

[45] Date of Patent: Aug. 20, 1991

[54] ROSE PLANT—MEIPIERAR VARIETY

[75] Inventor: Alain A. Meilland, Antibes, France

[73] Assignee: The Conard-Pyle Company, West Grove, Pa.

[21] Appl. No.: 483,020

[22] Filed: Feb. 21, 1990

[51] Int. Cl.[5] ..... A01H 5/00

[52] U.S. Cl. ..... Plt./15

[58] Field of Search ..... Plt./14, 15

[56] References Cited

U.S. PATENT DOCUMENTS

P.P. 5,846 1/1987 Meilland ..... Plt. 15

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive fully double large light cream yellow blossoms which initially exhibit a perfect bud configuration. Such blossoms are long lasting and the petals drop off cleanly. The plant exhibits an upright growth habit, forms very vigorous vegetation, and is well suited for use as a decorative planting when grown in parks and gardens. Additionally, the plant exhibits good disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Johnago variety (non-patented in the United States). The male parent (i.e., the pollen parent) was the Meikinosi variety (non-patented in the United States). The Meikinosi variety sometimes is known as the Tchin-Tchin variety. The parentage of the new variety can be summarized as follows:

Johnago × Meikinosi.

The seeds resulting from the above pollination were sown and 55 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive long lasting fully double large light cream yellow blossoms which initially exhibit a perfect bud configuration,
(b) exhibits an upright and bushy growth habit,
(c) is well adapted for growing in parks and gardens,
(d) exhibits very vigorous vegetation, and
(e) exhibits good disease resistance.

The new variety well meets the needs of the horticultural industry for all uses and is particularly well suited for use as a decorative planting in parks and gardens.

The new variety has been found to undergo asexual propagation by a number of routes, including budding, grafting, cuttage, etc. The characteristics of the new variety have been found to be stable and are strictly transmissible by such asexual propagation from one generation to another.

The new variety has been named the Meipierar variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were two years of age and were observed during September while budded on *Rosa froebelli* understock and growing at LeCannet des Maures, Var, France.

DETAILED DESCRIPTION

Figures 1, 2, 3, 4, 5, 6, 7, 8, 9, 10, 11, 12, 13, 14, 15, 16:
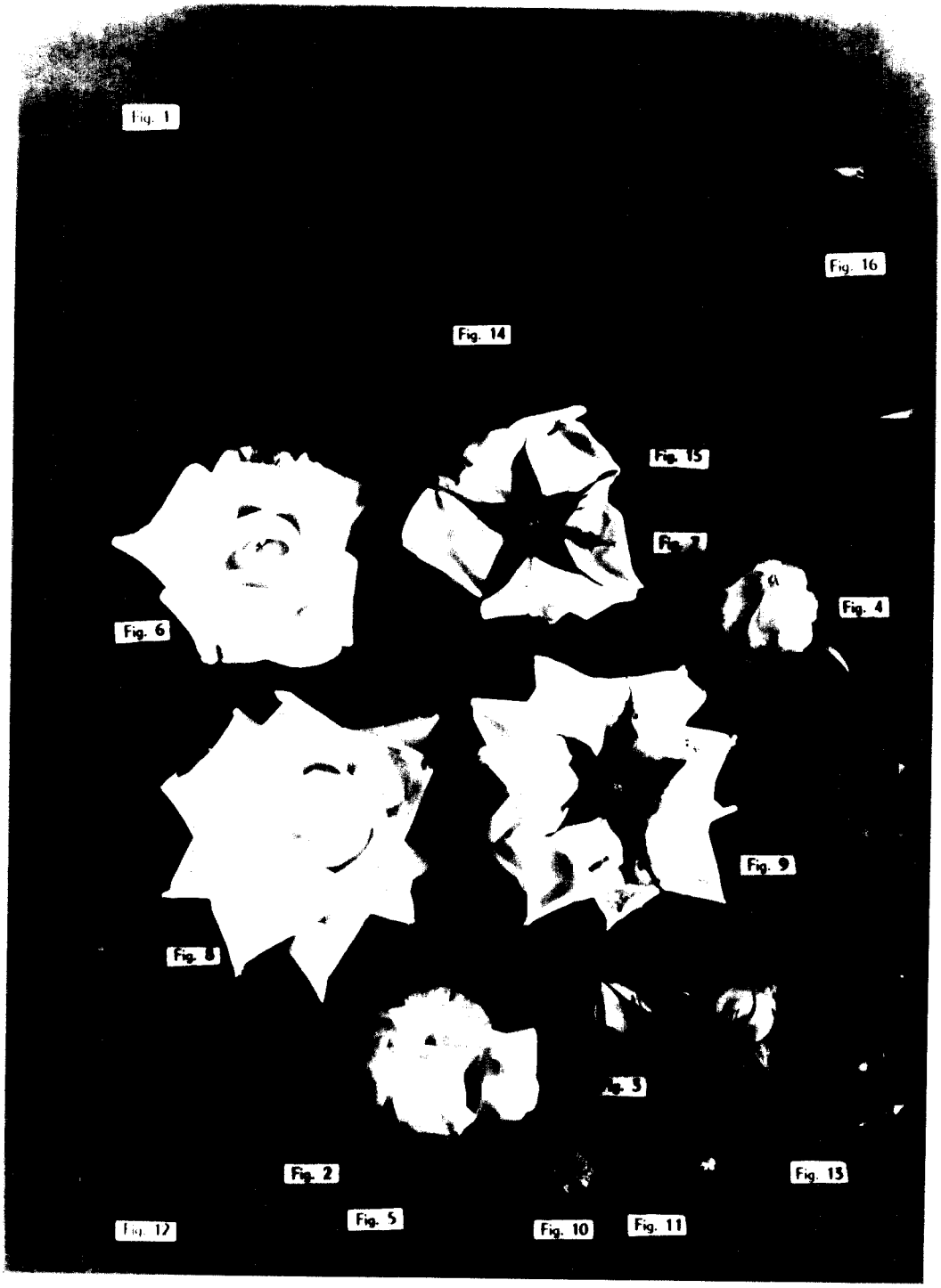
FIG. 1 illustrates a specimen of a young shoot.
FIG. 2 illustrates a specimen of a floral bud before the opening of the sepals.
FIG. 3 illustrates specimens of two floral buds at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower—plan view—obverse.
FIG. 7 illustrates a specimen of a fully open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates specimens of two flowering stems.
FIG. 13 illustrates a specimen of a main branch.
FIG. 14 illustrates a specimen of a leaf with three leaflets—plan view—under surface.
FIG. 15 illustrates a specimen of a leaf with five leaflets—plan view—upper surface.
FIG. 16 illustrates a specimen of a leaf with seven leaflets—plan view—upper surface.

The chart used in the identification of the colors is that of The Royal Horticultural Society (R.H.S. Colour Chart). The description is based on the observation of two year old plants made during September while budded on *Rosa froebelli* understock and growing at LaCannet des Maures, Var France. The coloration in common terms precedes reference to the chart.

Class: Hybrid Tea

Plant:

*Height.*—Approximately 80 to 90 cm. on average.

*Habit.*—Upright.

Branches:

*Color.*—Young stems: lettuce green, Yellow-Green Group 144B. Adult wood: light green, Yellow-Green Group 143C.

*Thorns.*—Size: large. Quantity: average. Color: pinkish on young wood and greenish changing to brown on adult wood.

Leaves:

*Stipules.*—Adnate, pectinate, very wide and linear.

*Petioles.*—Upper surface: striped reddish brown on young foliage and medium green on adult foliage with more or less glandular edges. Under surface: light green, bear numerous tiny prickles.

*Leaflets.*—Number: 3, 5 (most often), and 7. Sometimes the first pair of leaves is incompletely formed. Shape: oval. Serration: single and regular. Texture: leathery. General appearance: dense semi-dull foliage. Color (young foliage): Upper surface: reddish brown. Under surface: reddish brown. Color (adult foliage): Upper surface: bronze green, Yellow-Green Group 146A, more or less tinted with reddish coloration. Under surface: medium green, Yellow-Green Group 146B.

Inflorescence:

*Number of flowers.*—Generally one per stem, and sometimes two per stem.

*Peduncle.*—Straight, rigid, medium green and more or less tinted with reddish coloration, bears numerous pendiculate glands. The length is approximately 5.5 cm. on average.

*Sepals.*—Upper surface: tomentose, greenish and more or less tinted with reddish coloration. Under surface: medium green and more or less tinted with reddish coloration, the edges of the outer sepals are glandular and appendiculated.

*Buds.*—Shape: conical. Length: approximately 3 cm. on average. Size: large. Color upon opening: Upper surface: light yellow, Yellow Group 9D, and lighter on the edge. Under surface: light yellow, Yellow Group 9D, and lightly edged in pink.

*Flower.*—Shape: as a shallow cup and very double. Diameter: approximately 11 to 11.5 cm. on average. Color (when opening begins): Upper surface: light cream yellow, Yellow Group 8D, and more pronounced at base. Under surface: light cream yellow, Yellow Group 8D, and more pronounced at base. Color (when blooming): Upper surface: light cream yellow, Yellow Group 8D, and more pronounced at base. Under surface: light cream yellow, Yellow Group 8D, and more pronounced at base. Color (at end of opening): Upper surface: cream white, Yellow-White Group 158D. Under surface: cream white, Yellow-White Group 158D. Fragrance: none. Lasting quality: long. Petal number: approximately 40 to 45 on average. Texture: consistent. Petal shape: rounded with recurved edges. Petal drop: good. Stamen number: approximately 305 to 312 on average. Anthers: ochre and normal. Filaments: orange yellow and very irregular in height. Pistils: approximately 180 to 196 on average. Stigmas: normal and strawlike in coloration. Styles: fuschia with a strawlike base. Receptacle: light green, smooth, in longitudinal section it is in the shape of a wide pitcher.

Development:

*Vegetation.*—Strong and vigorous.

*Blooming.*—Excellent capacity for reblooming.

*Aptitude to bear fruits.*—Poor.

*Resistance to diseases.*—Good.

I claim:

1. A new and distinct variety of Hybrid Tea rose plant characterized by the following combination of characteristics:

(a) forms in abundance attractive long lasting fully double large light cream yellow blossoms which initially exhibit a perfect bud configuration,
(b) exhibits an upright and bushy growth habit,
(c) is well adapted for growing in parks and gardens,
(d) exhibits very vigorous vegetation, and
(e) exhibits good disease resistance;

substantially as herein shown and described.

* * * * *